US00PP10982P

United States Patent [19]

D'Ercole et al.

[11] Patent Number: Plant 10,982

[45] Date of Patent: Jun. 29, 1999

[54] STRAWBERRY PLANT NAMED 'IDEA'

[75] Inventors: Nicola D'Ercole, Bologna; Walther Faedi, Casena; Pasquale Rosati, San Lazzaro di Saven, all of Italy

[73] Assignee: E.R.S.O. Cooperative Company, Cesena, Italy

[21] Appl. No.: 08/773,249

[22] Filed: Dec. 23, 1996

Related U.S. Application Data

[63] Continuation of application No. 08/563,889, Nov. 22, 1995, abandoned, which is a continuation of application No. 08/349,217, Dec. 5, 1994, abandoned.

[51] Int. Cl.[6] ..... A01H 5/00

[52] U.S. Cl. ..... Plt./208

[58] Field of Search ..... Plt./48, 208, 209

[56] References Cited

U.S. PATENT DOCUMENTS

P.P. 1,005 2/1951 Felton ..... Plt./48
P.P. 2,085 9/1961 Ulrich ..... Plt./48
P.P. 8,991 11/1994 Sanford et al. ..... Plt./48

*Primary Examiner*—Howard J. Locker

[57] ABSTRACT

A new and distinct variety of strawberry (species *Fragaria*) which is resistant to anthracnose (*Colletotrcum actatium*) is late ripening and has large conical berries with a bright orange-red color.

2 Drawing Sheets

BACKGROWUND OF THE INVENTION

This new cultivar, named 'Idea', was selected in 1986 in a cultivated area in Cesena, Italy from the progeny of a cross made in 1984 between Sel 79.12.13 × 'Etna'. The seed parent Sel 79.12.13 was a plant used only for its germplasm and was never released to the industry and is not the subject of a plant parent or application for a plant patent in the United States. The pollen parent 'Etna' has been trialed at USDA, Beltsville, MD and at Whately, Mass. but never distinguished itself to be released in the United States and is not the subject of a plant patent or application for a plant patent in the United State. 'Idea' has been asexually propagated by runner propagation, tissue culture and micropropagation. 'Idea' has been asexually propagated in nurseries in Central Europe including Italy and in the United Kingdom and also in Massachusetts in the United States. 'Idea' has been shown to be extremely stable in traditional plant propagation procedures for strawberries. There never has been a case reported of 'Idea' not being stable is nurseries and fruit production trials.

The 'Idea' variety id characteristically different from any other commercial variety in the United States today, including the California varieties. Its differentiating characteristics include its disease resistance, the lateness of fruiting, the berry color, and its large yield.

Comparison with Related Prior Art

The following are characteristics of 'Idea' as compared to 'Biomidon' (B), 'Holiday' (HOL), 'Honeoye' (HON) and 'Jewel' (J):

| | | 'IDEA' | B | HOL | HON | J |
|---|---|---|---|---|---|---|
| Habit | upright 1<br>Intermediate 2<br>Open 3 | 2 | 3 | 1 | 3 | 2 |
| Vigor | 1 to 5<br>Poor to High | 4 | 4 | 3 | 3 | 3 |
| Bed Uniformity | 1 to 5<br>Poor to High | 3 | 4 | 2 | 4 | 4 |
| Central Leaf Shape | Roundish 1<br>Elliptic/Round 2<br>Elliptic/Elongated 3 | 1 | 2 | 2 | 2 | 1 |
| Central Leaf | Angular 1<br>Concave 2 | 3 | 2 | 1 | 3 | 3 |

-continued

| | | 'IDEA' | B | HOL | HON | J |
|---|---|---|---|---|---|---|
| Section | Flat 3<br>Convex 4 | | | | | |
| Teeth Shape | Pointed 1<br>Rounded 2 | 2 | 2 | 1 | 2 | 1 |
| Teeth Size | Large 1<br>Small 2 | 1 | 2 | 1 | 1 | 1 |
| Teeth Number | High 1<br>Medium 2<br>Low 3 | 1 | 1 | 2 | 1 | 1 |
| Leaf Size | Large 1<br>Medium 2<br>Small 3 | 2 | 2 | 1 | 2 | 2 |
| Leaf Base | Round 1<br>Tapered 2 | 1 | 1 | 2 | 2 | 1 |
| Growth Habit | Straight 1<br>Upright 2 | 1 | 1 | 1 | 2 | 1 |
| Upper Leaf Surface | Clear Green 1<br>Dark Green 2 | 1 | 1 | 1 | 1 | 1 |
| Upper Leaf Surface Glossiness | High 1<br>Medium 2<br>Low 3 | 2 | 1 | 1 | 2 | 1 |

Comparison to Cultivars of U.S. Plant Pat. Nos. 1005 and 2,085

The following is a comparison of 'Idea' with the cultivars of U.S. Plant Pat. Nos. 1,005 and 2,085:

| | IDEA | #1,005 | #2,085 |
|---|---|---|---|
| Fruiting Season | Very Late | Early-Mid Season | Early-Mid Season |
| Color | Bright Orange Red | Glossy Bright Red | Bright Red |
| Shape | Blocky, conical | Uniformly conical | Globe, conical |
| Calyx | Embedded - not easily removed | Not noted | Slightly embedded - (snaps easily) |
| Internal Color | Very Light Pink | Red throughout | Deep, rich color |
| Aroma | Slightly aromatic | Not noted | Distinctly aromatic |
| Flavor | Sweet, pleasant taste medium-good strawberry flavor | Sweet, slightly tart | Pineapple flavor |
| Fruit | Fruit lays on | Heavy upright | Strong and upright |

-continued

| | IDEA | #1,005 | #2,085 |
|---|---|---|---|
| Stems | ground | | |
| Leaf Serrations | Rounded | Sharp | Sharp |
| Runner Production | Very numerous - 50–80 per mother | 15 or more per mother | Fairly numerous |
| Seeds/-Achenes | Slightly recessed | Non-conspicuous | Not noted |

DESCRIPTION OF THE INVENTION

Figure 1:
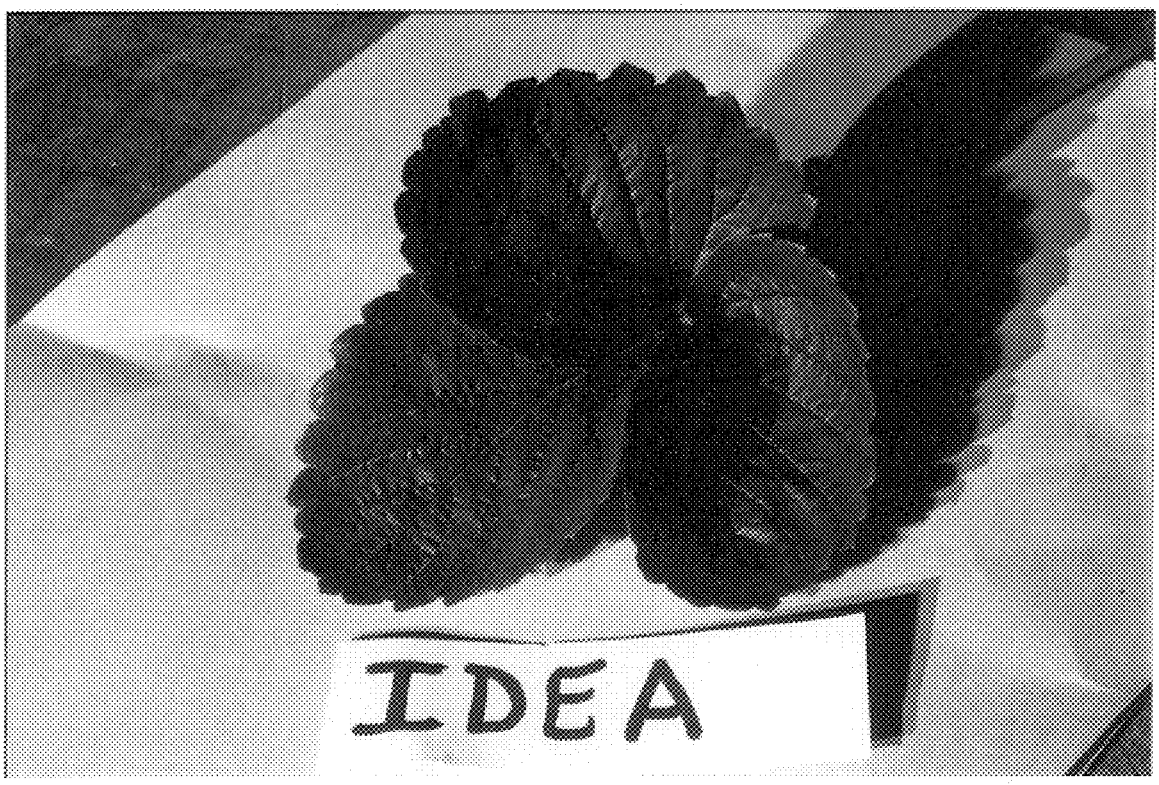
FIG. 1. shows the upper leaf surface of 'Idea'.
Figure 2:
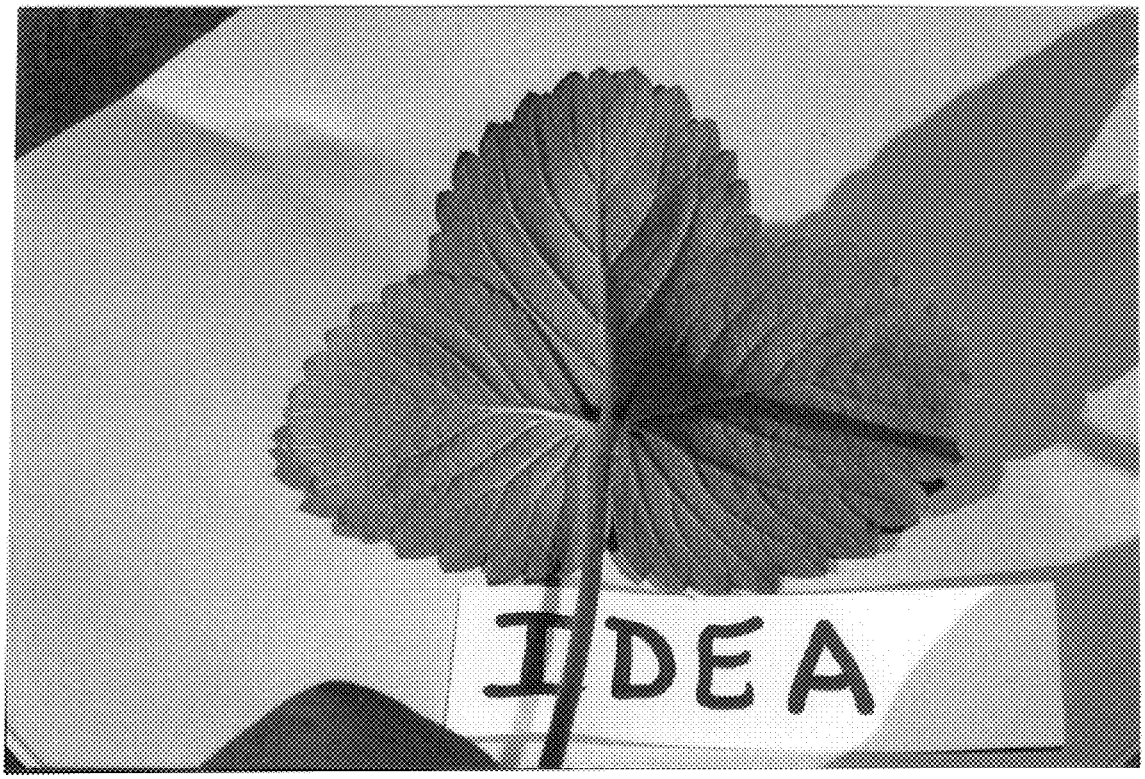
FIG. 2. shows the lower leaf surface of 'Idea'.
Figure 3:
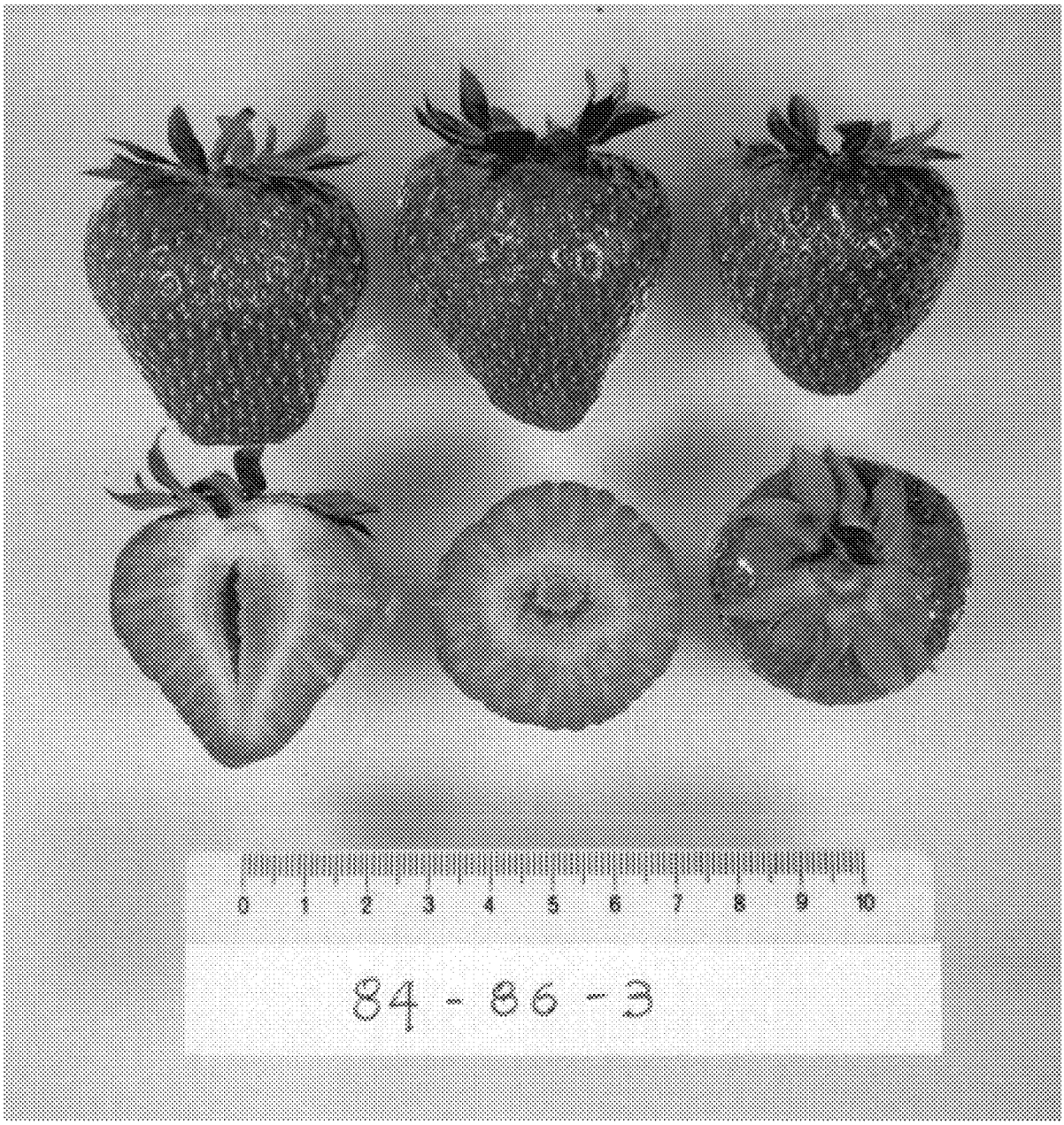
FIG. 3. shows the fruit of 'Idea'.

Strawberry 'Idea ' is a late ripening strawberry variety (season of the cv. 'Dana') with large conical beries having a bright orange-red skin color 5R, 5/10 (This color specification as well as the other color specifications employed in the description herein are those of the Munsell Color Chart for Plant Tissues, $2^{nd}$ edition, revised 1997.). The plant is highly vigorous, with terminal leaflets forming from obtuse to highly obtuse angles. Hairs on the petioles are perpendicular. Berries are large, conical, with an orange-red skin color, changes slightly recessed are or at skin surface level. It is a late ripening variety, June-bearing in the Italian Po valley and is not everbearing, It is resistant to most disease, in particular resistant to antracnose caused by *Colletotricum actatium*. 'Idea' is further described as follows:

1) *Habit.*—Expanded.
2) *Height.*—High.
3) *Maximum diameter.*—Large.
4) *Density.*—High.
5) *Vigor.*—High.

Leaf:

6) *Upper blade: main color.*—Clear green (green-yellow 7.5GY, 3/4).
7) *Upper blade: secondary color.*—Absent.
8) *Upper blade: brightness.*—Intermediate.
9) *Upper blade: outline.*—Flat or concave.
10) *Upper blade: curling.*—Scarce or medium.
11) *Vein emergence.*—Medium.
12) *Leaf margins.*—crenate to rounded serrate.
13) *Leaflets compared to the peduncle.*—Horizontal.
14) *Thickness.*—Medium.
15) *Upper blade pubescence.*—Scarce.
16) *Lower blade pubescence.*—Scarce.
16A) *Lower blade color.*—light green 7.5GY, 8/2.
17) *Leaflet number.*—Three, occasionally more than three.
18) *Terminal leaflet: length.*—Medium.
19) *Terminal leaflet: width.*—Medium.
20) *Terminal leaflet: length/width ratio.*—A little longer than wide.
21) *Terminal leaflet: basal angle.*—From obtuse to very obtuse.
22) *Terminal leaflet: basal shape.*—U shape.
23) *Terminal leaflet: teeth.*—Crenate.
24) *Terminal leaflet: secondary teeth.*—Occasional.

Petiole:

25) *Pebuscence.*—Medium high, fine and numerous.
26) *Hairs.*—Perpendicular.

Stipules:

27) *Red pigmentation.*—Scarce.
28) *Length.*—Medium.

Stolons:

29) *Number.*—High.
30) *Red pigmentation.*—Present, especially in the first part of the filament.
31) *Color.*—Red.
32) *Thickness.*—Thick.
33) *Pubescence.*—Scarce.
34) *Hair position.*—Perpendicular.

Flower cluster:

35) *Position compared to leaves.*—Under.

Peduncle:

36) *Length (flowers of third order).*—Medium-short.
37) *Thickness.*—Medium-high.
38) *Pubescene.*—Scarce.
39) *Hair position.*—Perpendicular.

Flowers:

40) *Sex.*—Hermaphrodite.
41) *Size.*—Medium-large.
42) *Calyx size related to corolla.*—Same size.
43) *Size of the upper calyx compared to the lower calyx.*—Same size.
44) *Calyx pubescence.*—Medium.

Petals:

45) *Number in primary flowers.*—From 5 to 8.
46) *Number in secondary flowers.*—From 5 to 6.
47) *Position of the margins.*—Overlapping.
48) *Length/width ratio.*—As long as wide.
49) *Basal angle.*—Obtuse.
50) *Undulation of the margins.*—Medium.

Anthers:

51) *Size.*—Medium-large.

Fruit:

52) *Length.*—Medium.
53) *Width.*—High.
54) *Maximum length/width ratio.*—More wide than long.
55) *Dimensions.*—Large.
56) *Shape.*—early berries are generally blocky, slightly longer than wide, with a tendency toward being pointed whereas more mature berries are conical.
57) *Difference in shape (between primary/secondary).*—Very high.
58) *Apex.*—Flat or round.
59) *Area without achenes.*—Small or medium.
60) *Ribs.*—Medium or scarce.
61) *Color.*—Red-orange.
62) *Color intensity.*—High.
63) *Color inensity.*—High.
64) *Brightness.*—High.
65) *Achenes position.*—Slightly recessed or at berry surface level.
66) *Calyx position.*—Quite immersed.
67) *Sepals.*—Slightly reflexed.
68) *Calyx size compared to fruit diameter.*—Smaller.
69) *Easy of calyx detachment.*—Medium.
70) *Flesh: firmness.*—High.
71) *Flesh: color.*—Clear red.
72) *Flesh: uniformity of color.*—Quite uniform.
73) *Flesh: sweetness.*—Medium.
74) *Flesh: acidity.*—Medium.

75*Flesh: flavor.*—Medium-good.
76) *Flesh; heart.*—Medium-large.
77) *Evidence of vascular bundles.*—Medium.
Flowering season:
78) 50% *of primary flowers open.*—Late.
Harvest season:
79) 50% *of the plants with ripe fruit.*—Late.
80) *Everbearing?*—Non everbearing.

Further characteristic of 'Idea' with reference to production in Whately, Mass. are as follows:

81) *Fruit weight.*—First pick: 37–41 grams/berry; average weight of season: 19–22 grams/berry.
82) *Fruit yield.*—About 30,000 pounds per acre.
83) *Picking season begins.*—June 25–28.
84) *Picking season ends.*—July 15–18.
85) *Leaf length.*—Average of 7.7 cm.
86) *Leaf width.*—Average of 7.2 cm.
87) *Leaf margin.*—Rounded serrations measuring 0.5 cm wide at the base for each.
88) *Peitole length.*—For mature leaves, a range of 20.3 to 26.5 cm.
89) *Stolons per plant.*—50–80 (range will vary with soil type, fertility and variations in management).
90) *Bloom coloration.*—Not a distinguishing characteristic.

Usefulness

This new cultivar is particularly well-suited for use by commercial fruit growers in areas similar to climate to the Italian Po Valley and to nothern areas (equivalent to Zones 4a to 6b). It is a late ripening variety which is disease resistant and particularly resistant to anthracnose (*Colletotricum actatium*).

What is claimed:

1. A new and distinct strawberry cultivar as herein described and illustrated.

* * * * *